(12) United States Patent
Martinez et al.

(10) Patent No.: US 12,150,758 B2
(45) Date of Patent: Nov. 26, 2024

(54) WATERPROOF ELECTRONIC DECALS FOR WIRELESS MONITORING OF BIOFLUIDS

(71) Applicant: Purdue Research Foundation, West Lafayette, IN (US)

(72) Inventors: Ramses Valentin Martinez, West Lafayette, IN (US); Aniket Pal, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 674 days.

(21) Appl. No.: 17/228,615

(22) Filed: Apr. 12, 2021

(65) Prior Publication Data

US 2022/0061713 A1     Mar. 3, 2022

Related U.S. Application Data

(60) Provisional application No. 63/008,759, filed on Apr. 12, 2020.

(51) Int. Cl.
*H04Q 9/00* (2006.01)
*A61B 5/00* (2006.01)
(Continued)

(52) U.S. Cl.
CPC ........ *A61B 5/14539* (2013.01); *A61B 5/0002* (2013.01); *A61B 5/1491* (2013.01);
(Continued)

(58) Field of Classification Search
CPC . A61B 5/14539; A61B 5/0002; A61B 5/1491; A61B 5/6833; A61B 5/14517;
(Continued)

(56) References Cited

U.S. PATENT DOCUMENTS

| | | | |
|---|---|---|---|
| 2016/0007894 A1* | 1/2016 | Kahlman | G01N 21/59 600/323 |
| 2020/0037884 A1* | 2/2020 | Ishida | A61B 5/01 |

(Continued)

OTHER PUBLICATIONS

Adeleke, "Premium ethylcullulose polymer based architectures at work in drug delivery", International Journal of Pharmaceutics: X, 1, published Jul. 8, 2019 (Year: 2019).*

(Continued)

*Primary Examiner* — Matthew Kremer
*Assistant Examiner* — Jonathan Drew Moroneso
(74) *Attorney, Agent, or Firm* — Purdue Research Foundation

(57) ABSTRACT

A wearable sensor decal may include a flexible wrapper layer, an intermediate layer, and a porous film layer. A first plurality of electrodes may be deposited on the wrapper layer. A heating element may be conductivity coupled to the first plurality of electrodes. A second plurality of electrodes may be deposited on the intermediate layer. A biosensor may be conductively coupled to the second plurality of electrodes. The flexible film may be hydrophilic to allow biofluids pass to the biosensor and the wrapper layer may be hydrophobic to provide waterproofing to the biosensor and heating element. The heating element may be powered to reduce thermal variance in biosensor measurements.

15 Claims, 12 Drawing Sheets

(51) Int. Cl.
   *A61B 5/145*   (2006.01)
   *A61B 5/1491*  (2006.01)
   *A61B 5/1477*  (2006.01)
(52) U.S. Cl.
   CPC ............ *A61B 5/6833* (2013.01); *H04Q 9/00* (2013.01); *A61B 5/14517* (2013.01); *A61B 5/1477* (2013.01); *A61B 5/6801* (2013.01); *A61B 2562/04* (2013.01); *A61B 2562/164* (2013.01); *H04Q 2209/40* (2013.01); *H04Q 2209/43* (2013.01)
(58) Field of Classification Search
   CPC . A61B 5/1477; A61B 5/6801; A61B 2562/04; A61B 2562/164; A61B 2562/0209; A61B 5/14521; H04Q 9/00; H04Q 2209/40; H04Q 2209/43
   See application file for complete search history.

(56) References Cited

U.S. PATENT DOCUMENTS

| | | | | |
|---|---|---|---|---|
| 2020/0155047 | A1* | 5/2020 | Rogers | A61B 5/4266 |
| 2020/0268293 | A1* | 8/2020 | Gassler | A61B 5/14546 |
| 2020/0359906 | A1* | 11/2020 | Tanaka | G01K 13/20 |
| 2021/0364464 | A1* | 11/2021 | Heikenfeld | G01N 21/01 |

OTHER PUBLICATIONS

Mishra et al., "Wearable potentiometric tattoo biosensor for on-body detection of G-type nerve agents stimulants", Sensors and Actuators: B, 273, published Jul. 2, 2018 (Year: 2018).*
Ferrari et al., "Conducting polymer tattoo electrodes in clinical electro- and magneto-encephalography", npj Flexible Electronic, 4, published Mar. 17, 2020 (Year: 2020).*
Heredia-Guerrero et al., "Antimicrobial, antioxidant, and waterproof RTV silicone-ethyl cellulose composites containing clove essential oil", Carbohydrate Polymers, 192, published Mar. 18, 2018 (Year: 2018).*
Altemimi et al., "Critical review of radio-frequency (RF) heating applications in food processing", Food Quality and Safety, 3, published Apr. 10, 2019 (Year: 2019).*
Bariya, M. et al., Wearable sweat sensors. Nat. Electron. vol. 1, 160-171, Mar. 2018. https://doi.org/10.1038/s41928-018-0043-y.
Benjamin, F.B., Sweating Response to Local Heat Application. J. Appl. Physiol. vol. 5, 594-598. Apr. 1953. https://doi.org/10.1152/jappl.1953.5.10.594.
Chang, M.-C. et al., Multimodal Sensor System for Pressure Ulcer Wound Assessment and Care. IEEE Trans. Ind. Informatics vol. 14, No. 3, 1186-1196, Mar. 2018; published Dec. 11, 2017. https://doi.org/10.1109/TII.2017.2782213.
Dang, W. et al., Stretchable wireless system for sweat pH monitoring. Biosensors and Bioelectronics. vol. 107, 192-202, (2018); available online Feb. 10, 2018. https://doi.org/10.1016/j.bios.2018.02.025.
Fay, C. et al., Real-time sweat pH monitoring based on a wearable chemical barcode micro-fluidic platform incorporating ionic liquids. Sensors and Actuators B: Chem. 171-172, 1327-1334, (2012); available online Jul. 3, 2012. https://doi.org/10.1016/j.snb.2012.06.048.
Frazzoni, M. et al., Impedance-pH Monitoring for Diagnosis of Reflux Disease: New Perspectives. Dig. Dis. Sci. 62, 1881-1889, (2017). https://doi.org/10.1007/s10620-017-4625-8.
Hemalatha, R. et al., Evaluation of vaginal pH for detection of bacterial vaginosis. Indian Journal of Medical Research, vol. 138, Issue 3, 354-9 (2013).
Huang, W-D. et al., A flexible pH sensor based on the iridium oxide sensing film. Sensors and Actuators A: Physical, vol. 169, 1-11, (2011). https://doi.org/10.1016/j.sna.2011.05.016.
Khandalava, J. et al. Evaluating vaginal pH. Accuracy of two commercial pH papers in comparison to a hand-held digital pH meter. Journal of Reproductive Medicine, vol. 44, Issue 2, (1999).
Lee, H.-T. et al, Conductivity relaxation of polyaniline. Makromol. Chem, Macromol. Chem. Phys. vol. 194, 2443-2452 (1993). https://doi.org/10.1002/macp.1993.021940903.
McDonald, J.C. et al. Fabrication of microfluidic systems in poly(dimethylsiloxane). Electrophoresis vol. 21, 27-40 (2000). https://doi.org/10.1002/(SICI)1522-2683(20000101)21:1<27::AID-ELPS27>3.0.CO;2-C.
Montain, S.J. et al., Sweat Mineral-Element Responses during 7 h of Exercise-Heat Stress. International Journal of Sport Nutrition and Exercise Metabolism, vol. 17, 574-582 (2007). https://doi.org/10.1123/ijsnem.17.6.574.
Morris, D. et al., Bio-sensing textile based patch with integrated optical detection system for sweat monitoring. Sensors and Actuators B: Chem., vol. 139, 231-236 (2009). https://doi.org/10.1016/j.snb.2009.02.032.
Niarchos, G. et al., Humidity Sensing Properties of Paper Substrates and Their Passivation with ZnO Nanoparticles for Sensor Applications. Sensors, vol. 17, 516. (2017). https://doi.org/10.3390/s17030516.
Pal, A. et al. Self-Powered, Paper-Based Electrochemical Devices for Sensitive Point-of-Care Testing. Advanced Materials Technologies, vol. 2, 1700130 (2017). https://doi.org/10.1002/admt.201700130.
Pal, A. et al., Early detection and monitoring of chronic wounds using low-cost, omniphobic paper-based smart bandages. Biosensors and Bioelectronics, vol. 117, 696-705 (2018). https://doi.org/10.1016/j.bios.2018.06.060.
Pietrzak, K. et al., Antimicrobial properties of silver nanoparticles misting on cotton fabrics. Textile Research Journal, vol. 86, 812-822 (2016). https://doi.org/10.1177/0040517515596933.
Rahimi, R. et al., A low-cost flexible pH sensor array for wound assessment. Sensors and Actuators B: Chem., vol. 229, 609-617 (2016); available online Dec. 30, 2015. https://doi.org/10.1016/j.snb.2015.12.082.
Rose, C. et al., The Characterization of Feces and Urine: A Review of the Literature to Inform Advanced Treatment Technology. Critical Reviews in Environmental Science and Technology, vol. 45, 1827-1879 (2015). https://doi.org/10.1080/10643389.2014.1000761.
Singh, R. et al., Dielectric spectroscopy of doped polyaniline. Synthetic Metals, vol. 104, 137-144 (1999). https://doi.org/10.1016/S0379-6779(99)00043-0.
Soares, B.G. et al., Dielectric behavior of polyaniline synthesized by different techniques. European Polymer Journal, vol. 42, 676-686 (2006); available online Oct. 3, 2005. https://doi.org/10.1016/j.eurpolymj.2005.08.013.
Sukitpaneenit, P. et al., Electrical conductivity and mechanical properties of polyaniline/natural rubber composite fibers. Journal of Applied Polymer Science, vol. 106, 4038-4046 (2007). https://doi.org/10.1002/app.27101.
Sun, K.-H. et al. Evaluation of in vitro and in vivo biocompatibility of a myo-inositol hexakisphosphate gelated polyaniline hydrogel in a rat model. Scientific Reports, vol. 6, 23931 (2016). https://doi.org/10.1038/srep23931.
Zhang, Q. et al., Characterization of Temperature Profiles in Skin and Transdermal Delivery System When Exposed to Temperature Gradients In Vivo and In Vitro. Pharm. Res., vol. 34, 1491-1504 (2017). https://doi.org/10.1007/s11095-017-2171-x.

* cited by examiner

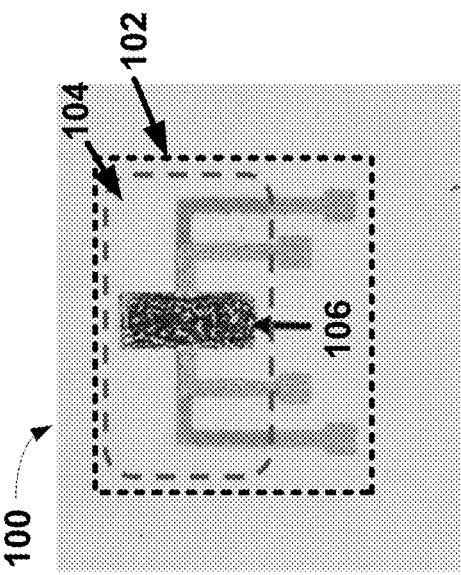 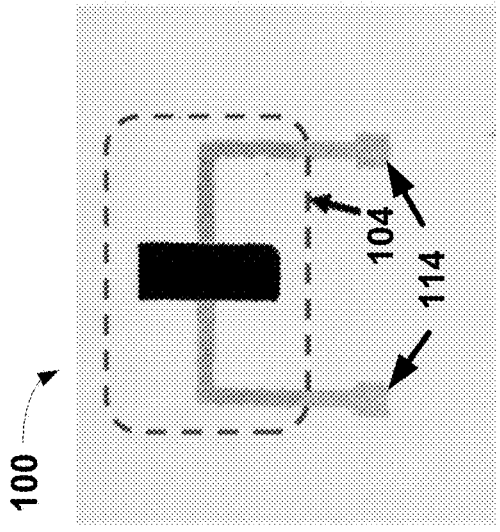 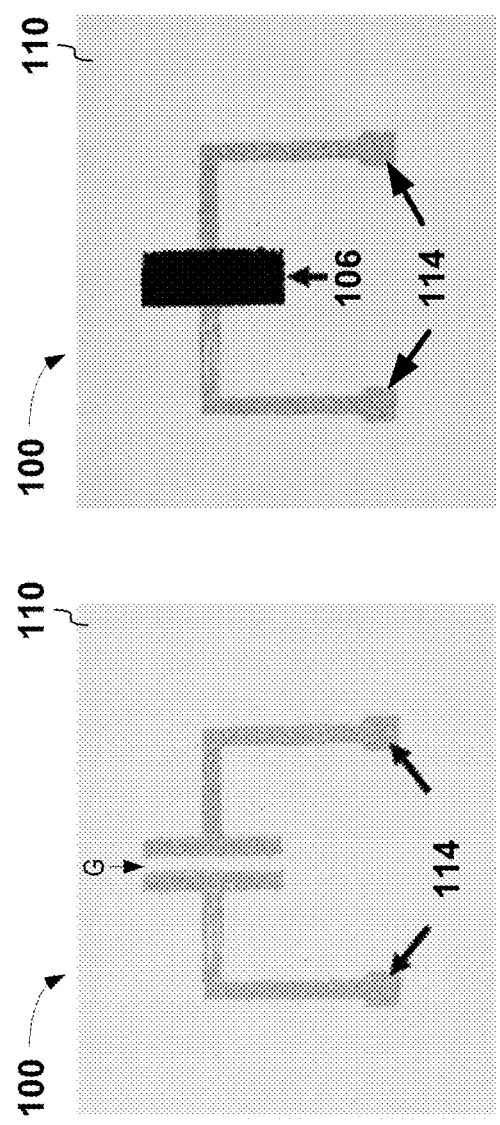 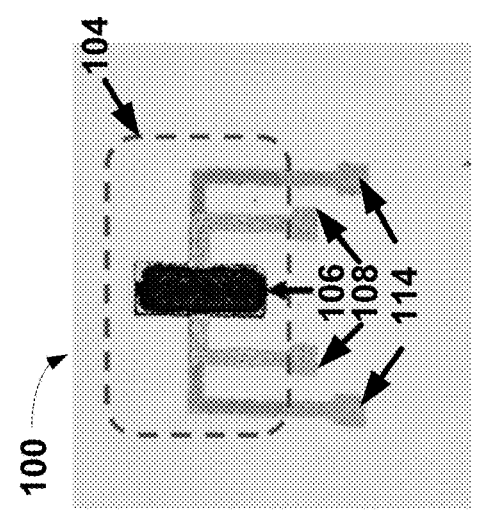 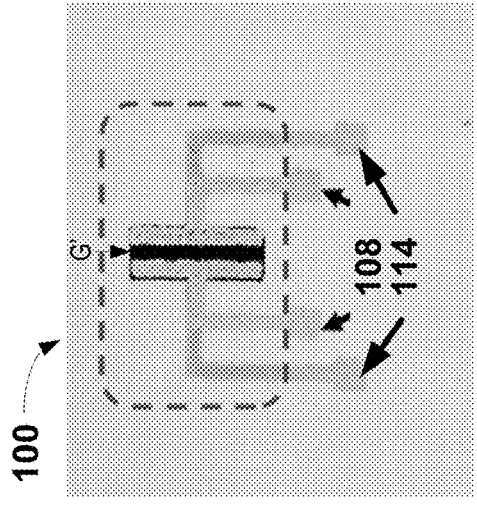

WATERPROOF ELECTRONIC DECALS FOR WIRELESS MONITORING OF BIOFLUIDS

CROSS REFERENCE TO RELATED APPLICATIONS

This application claims the benefit of U.S. Provisional Application No. 63/008,759 filed Apr. 12, 2020, the entirety of which is incorporated by reference.

TECHNICAL FIELD

This disclosure relates to wearable sensors and, in particular, to waterproof electronic decals.

BACKGROUND

Wearable sensors, such a waterproof electronic decal (WPED), monitor physiological signals such as breathing and heart rates, temperature, or muscular activity due to their simple acquisition methods. Wearable chemical sensors may provide noninvasive quantification of a variety of biomarkers on sweat and tears. Wearable sensors rely on the change of their electrical properties, such as capacitance or resistance, when in contact with the target analyte. The prolonged use of these sensors on skin, however, can lead to irritation and allergies due to their limited breathability and the constant contact between skin and metals. Furthermore, environmental moisture, variations in temperature, and the saturation of the sensing area often increase the variability of measurements of electrical chemical sensors, compromising their accuracy. Furthermore, the cost of wearable chemical sensors is often too high for single use applications, especially for at home testing or point of care diagnostics, due to the costly materials and manufacturing techniques required for their fabrication, as well as the expensive electronics required to acquire the measurements.

BRIEF DESCRIPTION OF THE DRAWINGS

The embodiments may be better understood with reference to the drawings and description. The components in the figures are not necessarily to scale. Moreover, in the figures, like-referenced numerals designate corresponding parts throughout the different views.

FIGS. 2A-F illustrates examples of a wearable sensor at various stages of manufacture;

DETAILED DESCRIPTION

While continuous monitoring of pH has demonstrated to be an effective technique to monitor an individual's health state, the design of wearable biosensors is subject to various challenges, such as high fabrication costs, thermal drift, sensitivity to moisture, and the limited applicability for users with metal allergies. The WPED may provide highly conformable, disposable biosensors capable of monitoring various biomarkers under a control temperature environment.

Aspects of the sensor, system, and methods descried herein provide numerous technical advancements. For example, the wearable sensor, also referred to as a waterproof electronic decal (WPED), may include a polyaniline/silver microflakes sensing layer optimized for accurate impedance based biomarker quantification across the clinically relevant range of most biofluids. Alternatively or in addition, the WPEDs may provide a heating that serves to stimulate sweating and/or prevent saturation of the sensing area, reducing the variability of the measurements. The conformability of WPEDs may enable simple and allergy-free attachment to skin, where it can monitor biomarkers, such as pH. Alternatively, the WPED may attach to the surface of sanitary tampons or to the surface of paper-based sample containers, for the pH-based diagnosis of bacterial vaginosis. In various examples, the WPED is, self-adhesive, breathable, flexible, moisture insensitive, and able to maintain their accuracy under significant thermal stresses.

Aspects of the system and methods described herein also provide a cost-effective portable impedance analyzer to wirelessly transmits biomarker data in real time to a mobile device or server. An app and/or server with machine executable code may enable long term monitoring and telemedicine applications. Thus, inexpensive single use WPEDs and a reusable, wireless impedance analyzer may provide a wearable solution for real time monitoring of biomarkers and/or accurate at home diagnosis of bacterial vaginosis, improving the capabilities of current low cost, point of care diagnostic tests. Additional and alternative benefits, efficiencies, and improvements over existing approaches are made evident in the systems and methods described below.

Figure 1:
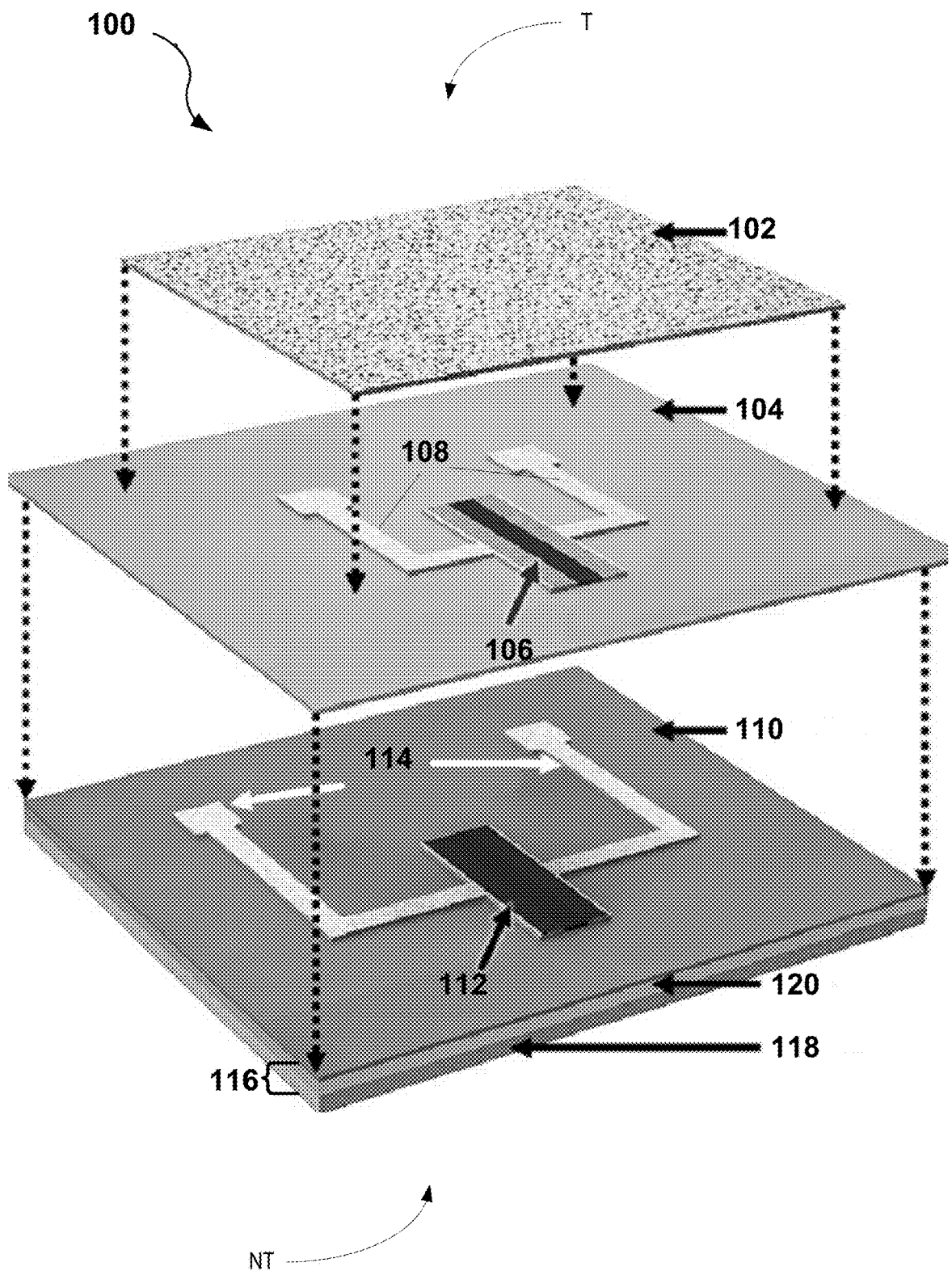
FIG. 1 illustrates a perspective view of a first example of a wearable sensor device.

FIG. 1 illustrates a perspective view of a first example of a wearable sensor device. The wearable sensor device may include a target surface side T and an non-target surface side NT. The target surface side T is the side of the wearable sensor device that comes into contact with a target surface for sensing. The non-target surface side NT is the side of the wearable sensor opposite of the target surface side T and which generally faces away from the target surface.

The wearable sensor 100 may include a porous film layer 102 on the target surface side T. The porous film layer 102 may include a flexible film that is attachable to deformable surfaces (such as the human skin and/or sanitary tampons). In some examples, the flexible film may be hydrophilic and/or porous. For example, the flexible film may allow biofluids and gas to pass through the layer. For example, the porous layer may have a pore size of ~0.5-1.0 µm. In various examples, the porous film may include a porous ethyl cellulous (pEC). The pEC may be attached to a variety of deformable surfaces (such as the skin of the user or sanitary tampons) and is capable of driving biofluids from its surface to other layers of the device (such as sensing or heating layers).

The wearable sensor may include an intermediate layer 104. The intermediate layer 104 may include a gas-permeable layer to facilitate release of gas while containing biofluids on the sensor. For example, the intermediate layer may include an ethyl cellulous (EC) sheet with additional components embedded or positioned on a surface of the layer. The intermediate layer may have a low porosity or at least a porosity less than the flexible layer 102.

The wearable sensor may include a biosensor 106 that reacts to biofluids to generate a physicochemical measurement. For example, the biosensor 106 may include a device that generates an electrical response based on presence of a biological analyte. For example, the biosensor may include a pH sensor. In pH sensing embodiments, the biosensor may include, for example, a polyaniline: silver microflakes (PANi/AgµF) composite. The biosensor may be at least partially positioned on the surface of the intermediate layer. Biofluids may pass through the porous layer and onto the biosensor.

The wearable sensor may include electrodes 108 for the biosensor (referred to as biosensor electrodes herein). The biosensor electrodes 108 may be positioned on a surface of the intermediate layer 104. The biosensor electrodes 108 may include conductors that couple to the biosensor 106. By way of example, the biosensor electrodes may include two Ag/AgCl electrodes printed on the intermediate layer. At least a portion of the biosensor may be positioned in a gap formed between the electrodes.

The wearable sensor 100 may further include a wrapper layer 110. The wrapper layer 110 may include a hydrophobic material to protect the device from environmental moisture and during water immersion. The wrapper layer 110 may be gas permeable to facilitate the release of gas evaporated at the sensing site. In addition, the wrapper layer 110 may include a transparent film. For example, the wrapper layer may include an EC/PDMS film.

The constituent material of the non-porous layers (104 and 110), ethyl cellulose, is permeable to most light gases and more importantly for us, to water vapor. The addition of PDMS to layer 110 makes it hydrophobic on top of being gas permeable. In various examples, the water vapor permeability of EC films with 5% PDMS may be $$\approx 2 \times 10^{-10} \frac{\text{g m}}{\text{m}^2 \text{s Pa}},$$

which, using the dimensions of WPEDs and the relative density of sweat, lead to a water vapor permeation rate of 0.1 µL/s. This rate is sufficient to match the rate of human sweat loss ( $$\left(12 - 120 \frac{\text{mL}}{\text{hour cm}^2}, \text{ or } 0.01\text{--}0.11 \text{ µL/s for the dimensions of } WPED\right).$$

or 0.01-0.11 µL/s for the dimensions of WPED).

The wearable sensor may a include a resistive heating element 112. The heating element 112 may include a resistive conductor that heats the wearable sensor, and/or the sensing area of the surface where the wearable sensor is attached. For example, the resistive heating element 112 may stimulate sweating and/or maintain dryness the to reduce the variability of the measurements, which is particularly important in pH sensing.

The wearable sensor may include electrodes for the heating element 112 (referred to as heating electrodes herein). The heating electrodes 112 may include conductors positioned on the surface of the wrapper layer 110. The conductors may each touch the heating element to power the heating element. In some examples, at least a portion of the heating element may be positioned in a gap formed in between the heating element. Alternatively, or in addition, the heating element may be printed on to a portion of the electrodes and surface area in between the electrodes. In some examples, the heating element may include Ag/AgCl ink printed on the wrapper layer 110

The wearable sensor may include a sacrificial layer 116 (or layers). The sacrificial layer 116 may assist with manufacturing, storage, and application of the device to a surface. Thus, the sacrificial layer may define the non-target surface NT side of the wearable sensor until the sacrificial layer is removed for application. For example, the sacrificial layer may include a paper-based layer 118 and/or a dissolvable layer 120. The dissolvable layer may include a dissolvable material, for example polyvinyl alcohol (PVA), to facilitate the manipulation and transfer of the device onto a surface. By way of example, the device may be placed on the skin of the user and the paper substrate is wetted with water, which dissolves the sacrificial PVA layer and releases the device on the skin of the user.

The features described herein provide various technical advantages. For example, the low thickness of the device (i.e. ~80 µm in some examples) and the hydrophilic behavior of the flex layer in contact with a surface readily secures the wearable sensor 100 to the surface user without any glue layer to prevent delamination. Alternatively or in addition, the wearable sensor 100 may readily conform to the surface of the skin without constraining the natural movements of the wearer, eliminating the somatosensory perception of these electronic decals. To detect bacterial vaginosis BV by monitoring vaginal pH, device may be attached to any conventional sanitary tampon. The flexibility, small thickness, and self-adhesion of the device may facilitate firm attachment to the surface of the tampon even after its significant expansion due to fluid saturation.

To effectively stimulate sweating, the heating element of the device may induce a localized heat stress over a time period (i.e. 38.5° C. for 3 mins) on the skin of the user. The microporous structure of the porous layer 102 may drive biofluids in contact with it to the biosensor 106 by capillary action. Additionally, the pore size (~0.5-1.0 µm) of the porous layer 102 prevents the measuring electrodes from coming in direct contact with the user, avoiding irritation and allergic reactions for users sensitized to metals.

In PH sensing examples, the biocompatibility of PANi and the antimicrobial properties of silver may also ensure that the device is consistent with epidermal and in-vivo applications. For example, once the biofluid reaches (i.e. sweat or vaginal fluid) reaches the PANi/AgµFs biosensor, the pH of the biofluid regulates the relative equilibrium between the polyaniline emeraldine salt (PANi-ES) and polyaniline emeraldine base (PANi-EB) states, proportionally modifying its conductivity, and allowing us to correlate the changes in impedance of the PANi/AgµFs composite to the pH value.

Most biofluids are good conductors of electricity and may compromise the accuracy of the impedance-based monitoring by short-circuiting electrodes, especially after long monitoring sessions. To maximize the stability of the biosensor 106 and enable reliable real-time monitoring over long periods of time, the heating element 112 over the bio-sensor may evaporate the analyte that has reacted with the biosensor, preventing a short-circuit. The fluid evaporated at the sensing area is released to the atmosphere through the porous structure of the breathable p-EC layer and the gas permeable intermediate layer. The outermost wrapper layer of the device may include a transparent, hydrophobic film (such as PANi/AgµFs) which protects the device from environmental moisture and during water immersion due to the hydrophobic properties of the PDMS.

FIG. 2A-F illustrates examples of the wearable sensor 100 at various stages of manufacture. Referring to FIG. 2A, the electrodes 114 for the heating element 112 may be screen printed onto the wrapper layer 110 to form a gap G between at least a portion of the electrodes 114. Referring to FIG. 2B, the heating element 112 may be applied to the gap G formed in between the electrodes 114 and, in some circumstances, a portion of both of the electrodes 114. The heating element 112 include, for example, carbon ink or some other ink-based conductor in cases where printing is used. Referring to FIG. 2C, the intermediate layer 104 may be applied on top of the heating element 112. As previously discussed, the intermediate layer 104 may include, in some examples, a transparent EC material. At least a portion of the heating electrodes 114 may be exposed and not covered by the intermediate layer 104. The exposed portions of the heating electrodes 112 may form contacts for interfacing with an external system (refer to FIG. 6 and related discussion).

Referring to FIG. 2D, the biosensor electrodes 108 may be applied on the intermediate layer to form a gap G' between at least a portion each electrode. The biosensor electrodes 108 may include Ag/AgCl ink or some other type of conductive printable ink. It should be appreciated that the biosensor electrodes 108 may be printed on both the intermediate layer 104 and the wrapper layer 110. Referring to FIG. 2E, the biosensor 106 may be applied to gap G' between the biosensor electrodes and, in some cases, onto the biosensor electrodes 108. The biosensor 106 may be positioned immediately above the heating element, but separated from the heating element by the intermediate layer 104. The intermediate layer 104 may insulate the heating element 112 and heating electrodes 114 from the biosensor 106 and biosensor electrodes 108.

Figure 3B:
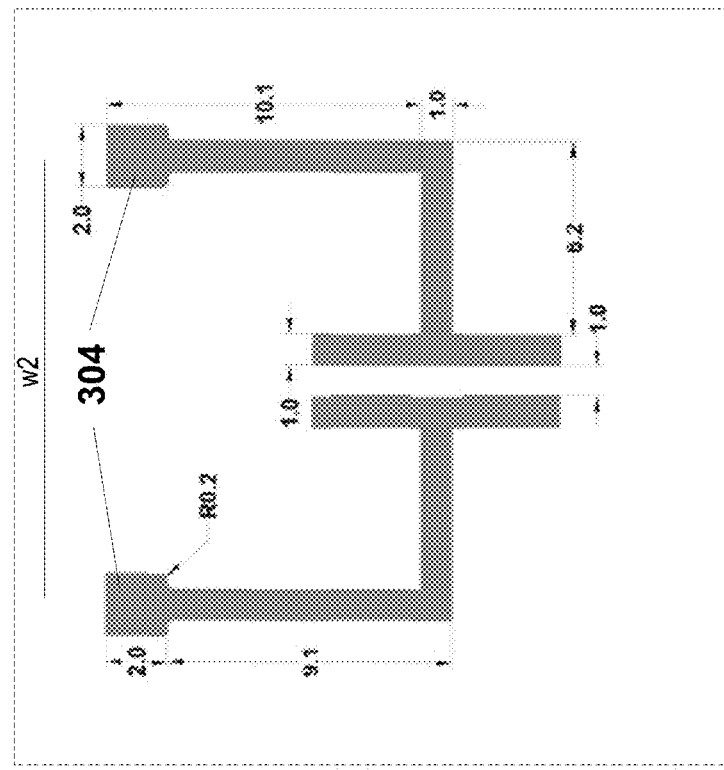
FIGS. 3A-B illustrate an example schematics for the electrodes and heating element of a wearable sensor.
Figure 3A:
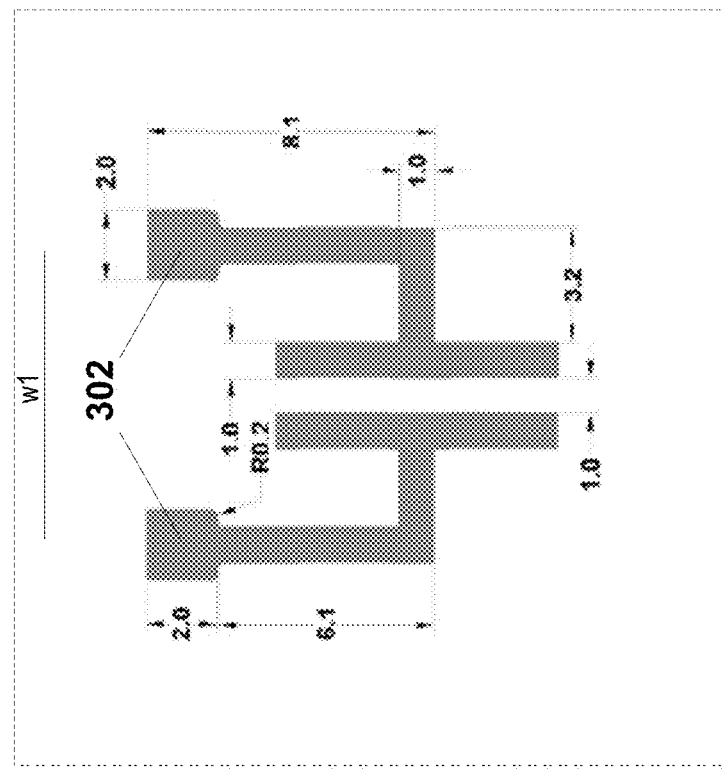

FIG. 3A-B illustrates an example schematic for the electrodes and heating element of the wearable sensor 100. FIG. 3A illustrates an example schematic for electrodes for the biosensor. FIG. 3B illustrates an example schematic for the electrodes used for the heating element. The dimensions shown in FIG. 3A-B dimensions are in mm. These dimensions are non-limiting, and are provided to show that the wearable sensor may include contacts with dimensions less than 10 MM. Other examples may have larger or smaller dimensions than presented.

The biosensor electrodes and/or the heating electrodes may each include a corresponding pair of contacts 302-304. The biosensor contacts 302 may connect to a spectrometer or some other type of electrical measurement requirement. The heater contacts 304 may connect to a power source. The width w1 between the biosensor contacts 302 of the biosensor may be greater (as in FIG. 3A-B) or lesser than the width w2 between the heater contacts. The contacts of the electrodes on the wearable sensor may be accesses in a variety of ways.

Figure 4:
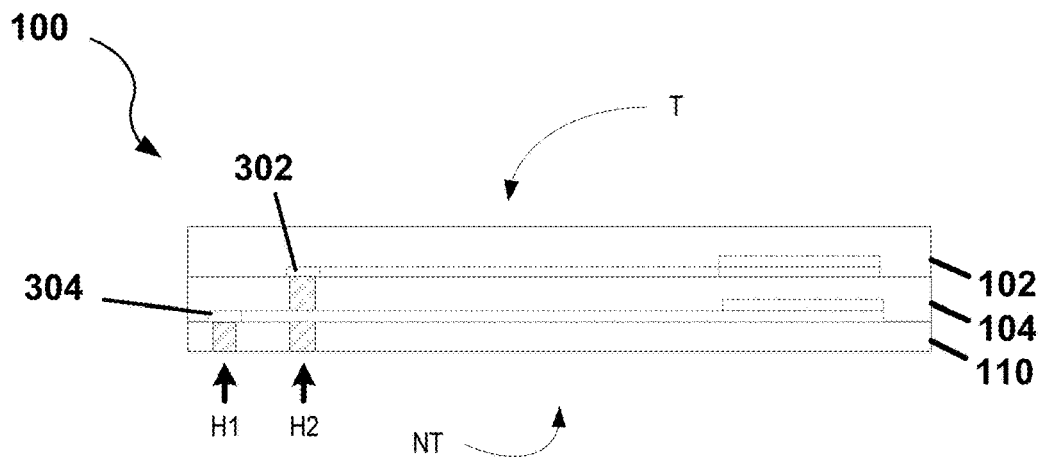
FIG. 4 illustrates a side view of a second example of a wearable sensor.

FIG. 4 illustrates a side view of a second example of the wearable sensor 100. The contacts 302-304 may include the biosensor contact 302 and the heater contact 304. To access the heater contacts 304, a portion of the wrapper layer 110 may penetrated and/or removed. For example, the wrapper layer 110 may be penetrated with an electrical lead that comes into contact with the heater contacts 304. Alternatively or in addition, a through hole h1 through the wrapper layer 304 immediately adjacent to the heater contact may be formed by removing a portion of the wrapper layer.

To access the biosensor contact 302, a portion of the wrapper layer 110 and intermediate layer 104 may be penetrated and/or removed. For example, both the wrapper layer 110 and intermediate layer 104 may be penetrated to access to the biosensor contact 302. Alternatively or in addition, a through hole h2 through the wrapper layer 110 and intermediate layer 104 immediately adjacent to the biosensor contact 302 may be formed by removing portions of the wrapper layer 110 and intermediate layer 104.

Figure 5:
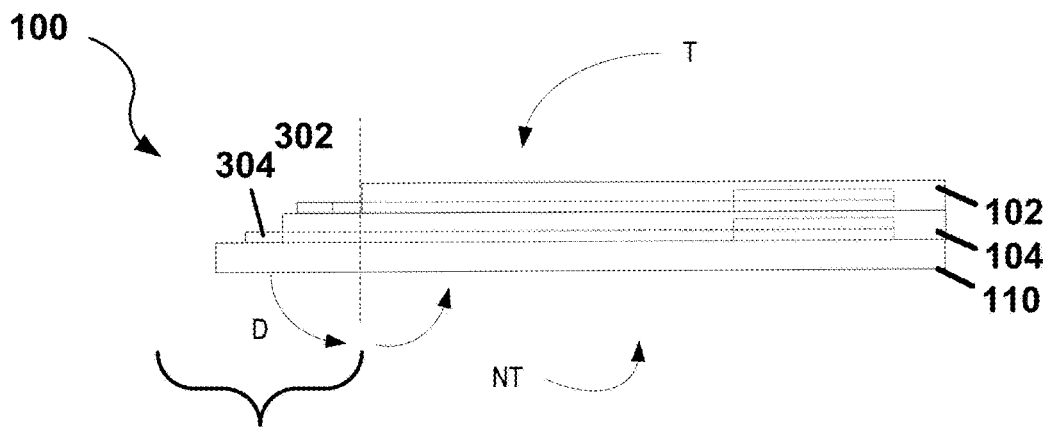
FIG. 5 illustrates a side view of an third example of a wearable sensor.

FIG. 5 illustrates a side view of a third example of the wearable sensor 100. In some examples, the biosensor contact 302 and heater contact 304 may remain exposed on the target surface side (T) of the wearable sensor. In other words, the porous layer 102 may not cover the biosensor contact 302 and the intermediate layer 104 may not cover the heater contact 304. The intermediate layer 104 may support the biosensor contacts 302 and the wrapper layer 110 may support the heater contact 304 and biosensor contacts 302.

During application, a foldable portion 502 of the wearable sensor 100 may be folded back to expose the contacts 402-404. The foldable portion 502 may include the contacts 402-404. The folded portion may fold in a direction D so that the wrapper layer in the folded portion wrapper layer 110 forms less than 180 degrees with a remainder of the wrapper layer 110.

Figure 6:
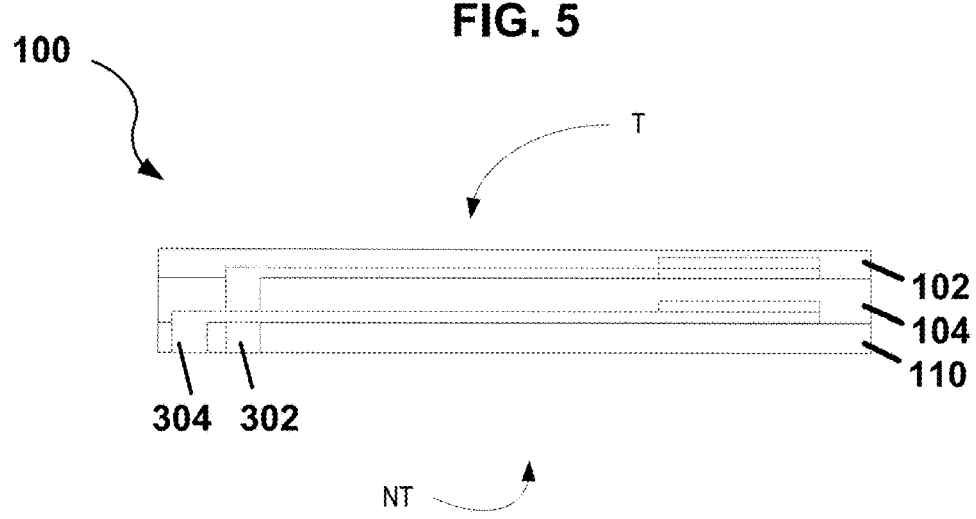
FIG. 6 illustrates a side view of a fourth example of a wearable sensor.

FIG. 6 illustrates a side view of a fourth example of the wearable sensor 100. The contacts 402-404 may be exposed on the non-target surface side (NT) of the wearable sensor 100. For example, the biosensor contact 302 may extend through the intermediate layer 104 and the wrapper layer 110 and the heater contact 304 may extend through the wrapper layer 110.

To accomplish this, through holes may be formed in the wrapper layer after the wrapper layer is deposited. Conductive ink for the heater electrodes may be printed in the through-holes to form the heater contacts. For the biosensor contacts, through holes may be formed in the intermediate layer and the wrapper layer. Then, conductive ink for the biosensor electrodes may be printed in the through holes to form the biosensor contacts.

Other ways of exposing the contacts 302-4304 are possible. For example, referring to FIG. 6, the biosensor contacts 304 may extend through the intermediate layer 104. The wrapper layer 110 may be punctured and/or portions of the wrapper layer 110 may be removed to expose the contacts 302-304.

Figures 7A, 7B:
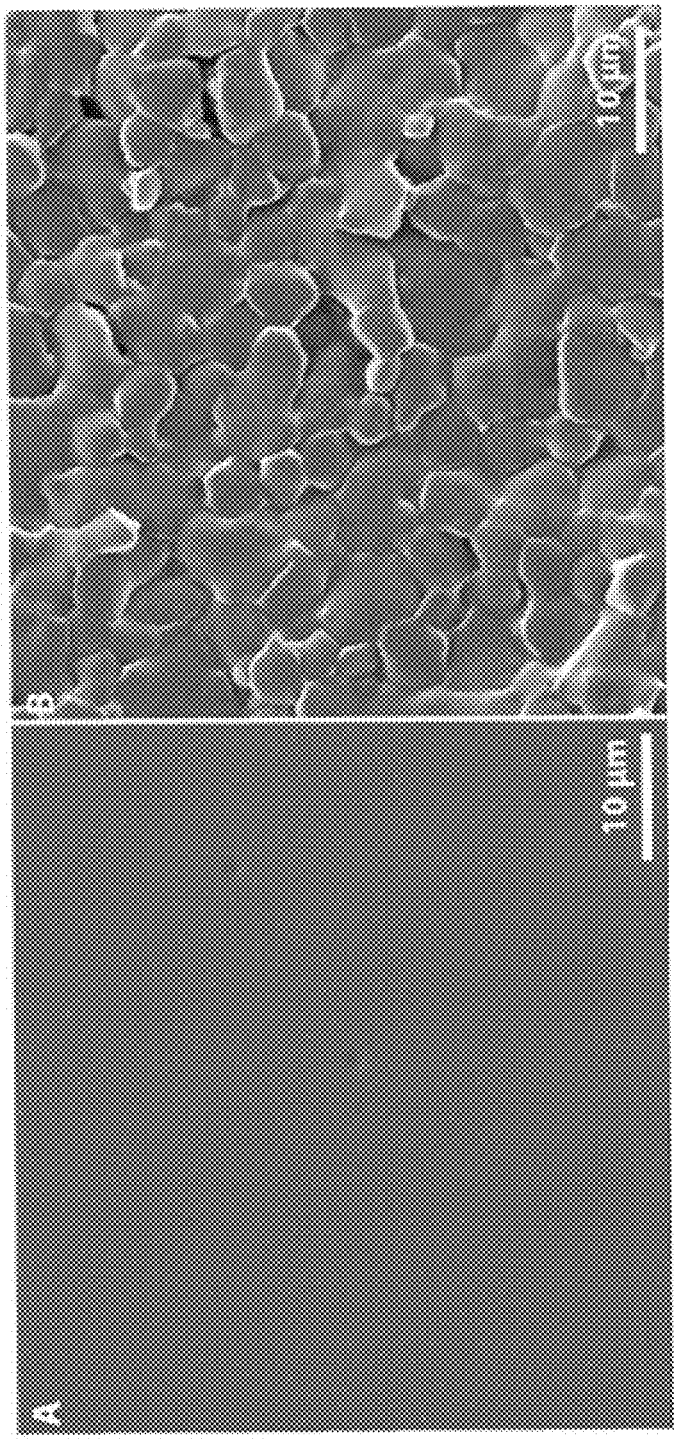
FIGS. 7A-B illustrate comparative examples of the smooth surface of a continuous EC film and a porous structure of a porous EC film.

FIGS. 7A-B illustrates comparative examples of the smooth surface of a continuous EC film (FIG. 7A) and the porous structure of a porous EC film (FIG. 7B). The creation of the microporous texture of the porous EC can be explained by considering the unequal evaporation rates of the ethanol water EC ternary system: the solvent for EC, ethanol, has a much faster evaporation rate than the non-solvent, water. As the ethanol evaporates quickly, the concentration of water increases, forcing the EC to form coacervates. As the evaporation continues, the coacervate droplets continue to grow until they form a gel like coagulated structure. When all the liquid evaporates, the gel dries into a xerogel with high porosity.

Figure 8A:
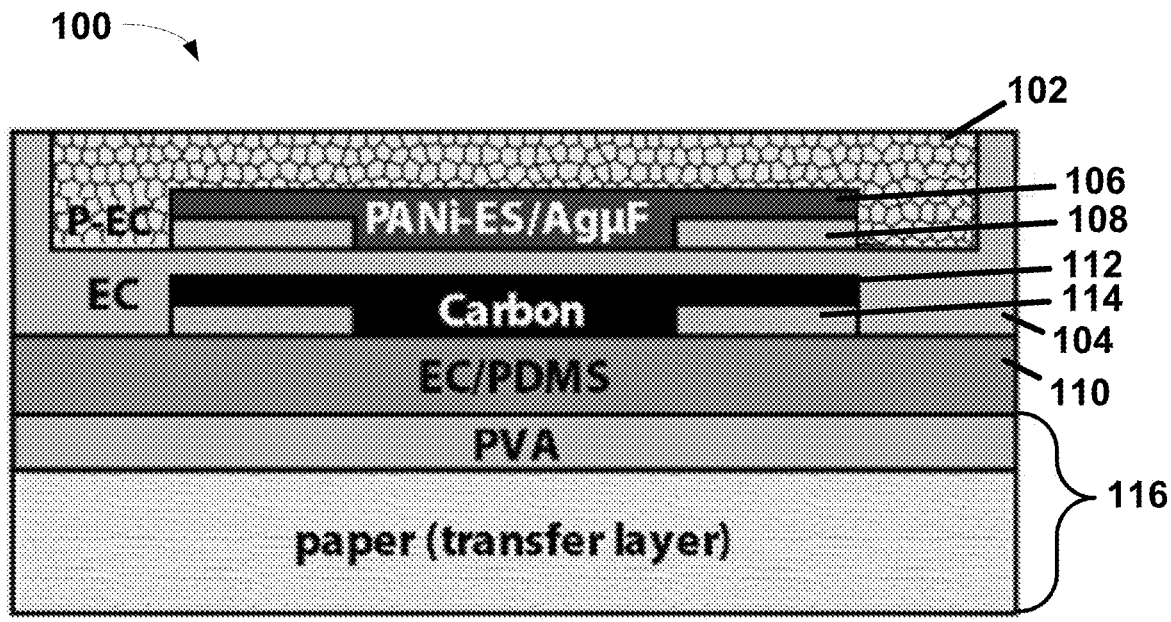
FIGS. 8A-B illustrate a cross sections of a fifth example of a wearable sensor.
Figure 8B:
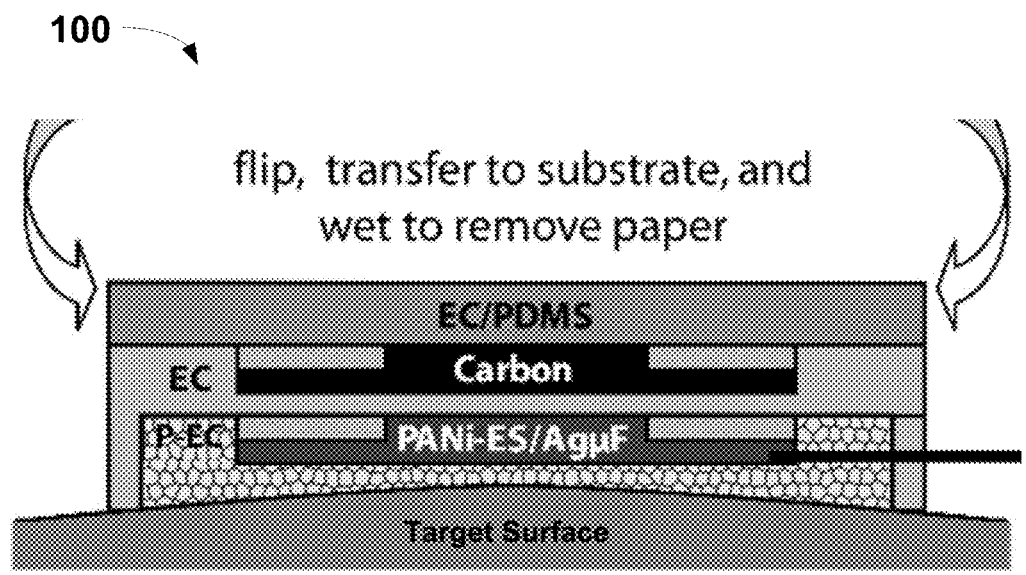

FIGS. 8A-B illustrates a cross section of a fifth example of the wearable sensor 100, before and after its transfer to a monitored surface. FIG. 8A illustrates a cross section of the wearable sensor 100 before transfer to a target surface. The sacrificial layer 116 may be formed by coating paper with PVA, which is dissolvable with water. EC and PDMS may be deposited on the sacrificial layer via printing or some any suitable deposition technique.

The wrapper layer 110 may receive the heating electrodes 114 for the heating element 112. The heating electrodes 114 may be positioned on the surface of the wrapper layer 110 such that a gap is formed between the heating elements. The heating electrodes 114 may also be referred to a heater electrode layer because it is deposited on top of the wrapper layer 110.

The wrapper layer 110 and/or the heating electrodes 114 may receive the heating element 112. The heating element 112 may be deposited onto the surface of the wrapper layer 110 in the gap formed by the heating electrodes 114. The heating element 112 may also be referred to as a heating element layer. Surfaces of the heating electrodes 112 substantially parallel to and raised from the surface of the wrapper layer 110 may also receive the heating element 112 to further increase conductive coupling.

The intermediate layer 104 may receive the electrodes 108 for the biosensor 106. The biosensor electrodes 108 may be positioned on a surface of the intermediate layer 104 and form a gap in between at least a portion of the electrodes 108. The biosensor electrodes 108 may also be referred to as the biosensor electrodes layer because they may be deposited on top of the intermediate layer 104. The biosensor 106 may be deposited onto the intermediate layer 104 in the gap defined between the electrodes 108. In some examples, the biosensor may be further deposited on top of the electrodes 108 to increase conductive coupling. The biosensor 106 may be referred to as the intermediate layer because it is deposited on top of the biosensor electrodes 108 and the intermediate layer 112.

The flexible film 102 may be deposited on the biosensor, electrodes and at least a portion of the intermediate layer. In some examples, the intermediate layer 104 may include a protrusion that defines a recess which receives the flexible film. At least a portion of the intermediate layer 104 along with the flexible film may form an outer surface of the wearable sensor 100, which is configured to be received by a target surface. The wearable sensor may be flipped such that the flexible layer 102 comes in contact with the target surface. Thereafter, the paper substrate may be wetted with water. The water may reach the dissolvable layer and the dissolvable layer may begin to dissolve enabling the paper to be removed. FIG. 2B illustrates a cross section of the wearable sensor 100 after transfer to a target surface. The target surface may include skin of a user, or some other service where biosensing is performed. In some implementations, the target surface may include sanitary tampons for the detection of their expansion due to fluid absorption. In such an example, two conductive threads, coiled around the strings of the tampon, and coated with PDMS, connect to the device with a flexible paper connector, which interfaces with a portable impedance analyzer.

Figure 9:
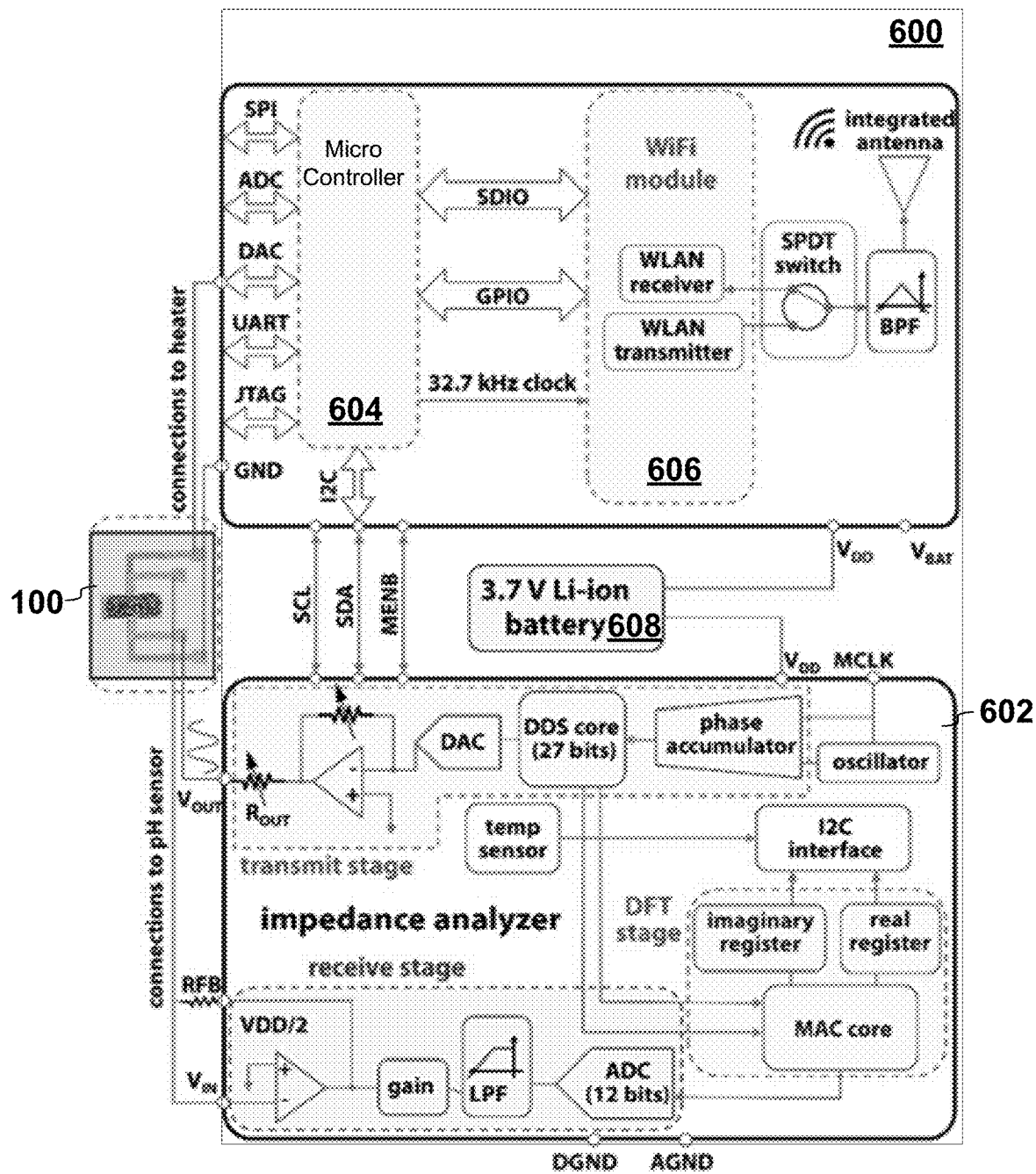
FIG. 9 illustrates an example of a system to interface with a wearable sensor.

FIG. 9 illustrates an example of a system 900 to interface with the wearable sensor 100. The system 900 may include an impedance spectrometer 902, a microcontroller 904, and a wifi module 906 and a power source 608. The power source 608 may include, for example, a lithium ion rechargeable battery or some other form of battery.

The impedance spectrometer 902 may connect to the biosensor electrodes of the wearable sensor. The impedance spectrometer 902 may measure electrical signals from the biosensor electrodes and generate electrical measurements, such as impedance. The microcontroller 904 may receive the receive the electrical measurements. Based on the electrical measurements, the microcontroller 904 may calculate biofluidic measurements.

The microcontroller 904 may conductivity connect to the heating electrodes to control the heating element. For example, the microcontroller may increase power to the heating element in response to various triggering conditions. For example, the microcontroller may receive a message to start detection model. The microcontroller may cause power to be supplied to the heating element for a pre-set amount of time. Alternatively or in addition, the microcontroller may repeatedly engage the heating element over an interval. In some examples, the microcontroller may receive a command to stop sensing and, in response, stop providing power to the heating element.

The microcontroller may communicate the biofluidic measurements to the WiFi module. The Wi Fi module may communicate the biofluidic measurements to a server, a mobile device, or a combination there. In some examples, the mobile device may include a user interface, sch as an App, which displays and stores the information. Alternatively or in addition, if the measurements are outside the clinically normal range, the microcontroller may encrypts and transfers the data to relevant care givers or other destinations.

The system 900 may be implemented with additional, different, or fewer components than illustrated. Each component may include additional, different, or fewer components. The microcontroller 904 may include a processor in communication with memory. In some examples, the microcontroller 904 may also be in communication with additional elements, such as the communication interfaces, the input interfaces, and/or the user interface. Examples of the microcontroller 904 may include a general processor, a central processing unit, logical CPUs/arrays, a microcontroller, a server, an application specific integrated circuit (ASIC), a digital signal processor, a field programmable gate array (FPGA), and/or a digital circuit, analog circuit, or some combination thereof.

The microcontroller 904 may be one or more devices operable to execute logic. The logic may include computer executable instructions or computer code stored in memory that when executed by the microcontroller, cause the microcontroller to perform the operations the system 900. The memory may be any device for storing and retrieving data or any combination thereof. The memory may include non-volatile and/or volatile memory, such as a random-access memory (RAM), a read-only memory (ROM), an erasable programmable read-only memory (EPROM), or flash memory. Alternatively, or in addition, the memory 820 may include an optical, magnetic (hard-drive), solid-state drive or any other form of data storage device.

Furthermore, although specific components are described above, methods, systems, and articles of manufacture described herein may include additional, fewer, or different components. For example, a microcontroller 904 may be implemented as a microprocessor, application specific integrated circuit (ASIC), discrete logic, or a combination of other type of circuits or logic. Similarly, memories may be DRAM, SRAM, Flash or any other type of memory. Flags, data, databases, tables, entities, and other data structures may be separately stored and managed, may be incorporated into a single memory or database, may be distributed, or may be logically and physically organized in many different ways. The components may operate independently or be part of a same apparatus executing a same program or different programs. The components may be resident on separate hardware, such as separate removable circuit boards, or share common hardware, such as a same memory and processor for implementing instructions from the memory. Programs may be parts of a single program, separate programs, or distributed across several memories and processors.

The low cost of the wearable sensor ensures that they can be deployed as single-use devices. For example, after monitoring, the user can delaminate one corner of the device with their nails and peel off the whole device (without causing skin irritation) and dispose it. BV-detecting device can be disposed along with the tampon once the measurements are completed. Upon incineration, the device may generate minimal amounts of solid byproducts. While the device may be single-use devices, the miniaturized impedance analyzer circuit can be reused multiple times with different wearable sensors and by different users.

The system 900 may be affixed in a conformable area of a user, such as a sweatband. This system may enable the wireless collection and transmission of biofluidic measurements using device without causing significant constraints to the natural movements of the wearer.

Figure 10:
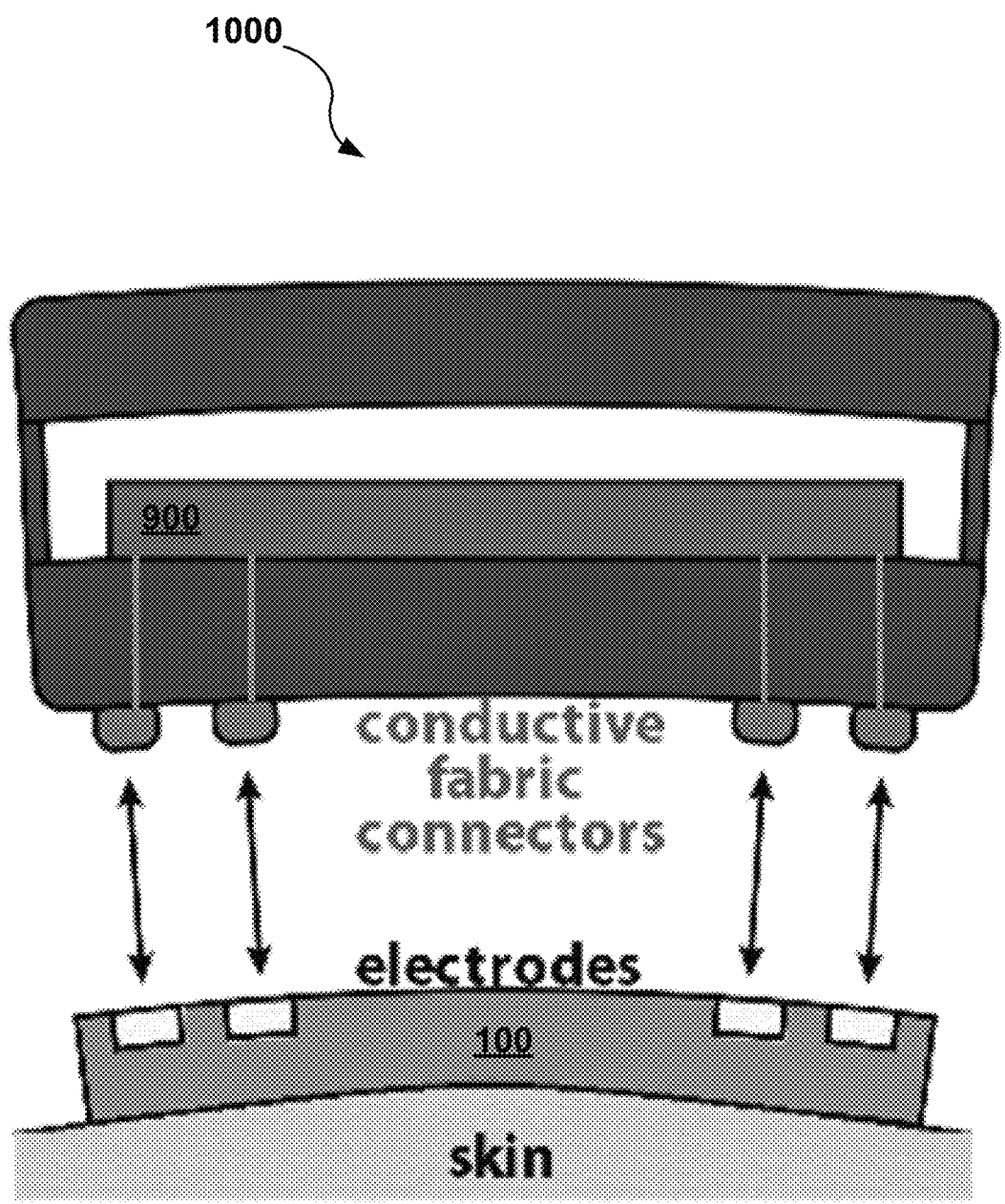
FIG. 10 illustrates an example of a wearable apparatus for a system.

FIG. 10 illustrates an example of a wearable apparatus 1000 for the system 900 and wearable sensor 100. The wearable apparatus 1000 may include connectors that are conductively coupled to the portable system. The connectors may include a first set of connectors that are positioned to connect with the biosensor electrodes. The connectors may include a second set of connectors that are positioned to connect with the heating element electrodes. The wearable apparatus 1000 may further include a hole to receive a strap that wraps around the target area of a subject, such as an arm or leg. When the armband is placed on the user, the connectors may be positioned over the electrodes of the wearable sensor.

The system described herein may enable at home performance of these tests. For example, tampons with the device attached can be worn as normal, taken out, and interfaced to the portable impedance analyzer for assessment (such as pH measurement). To connect the tampon mounted device with the circuitry, conductive threads may be coated with a hydrophobic material (i.e. PDMS) and then embroidered on the tampon, ending on a small paper-based connector for simple interfacing. The biocompatible hydrophobic coating prevents liquid absorption by the conductive threads, while the paper-based connector interfaces with the portable circuitry housed in a housing through copper clip connectors.

Figure 11:
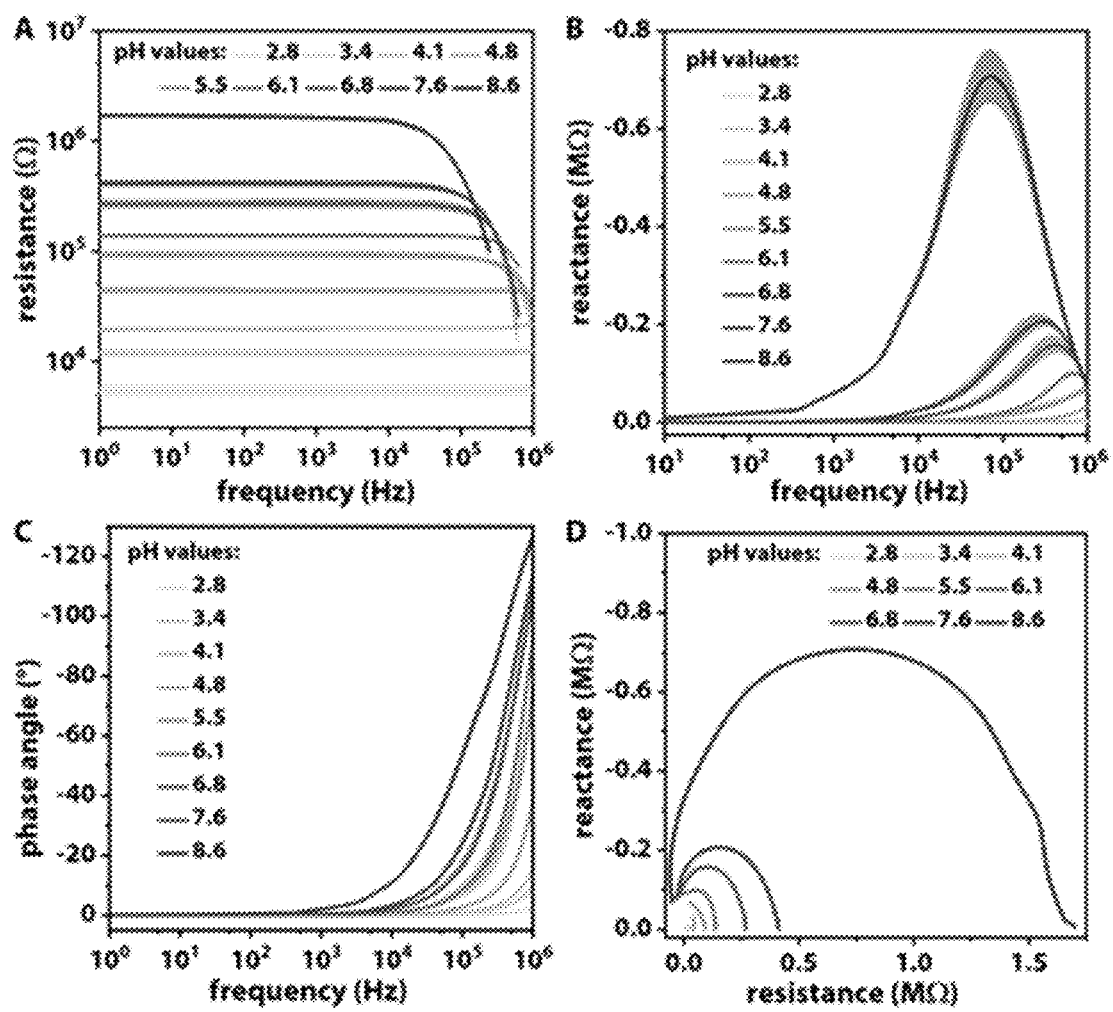
FIG. 11 illustrates an example of electrical performance of a pH biosensor for a wearable sensor.

FIG. 11 illustrates an example of electrical performance of a pH biosensor for the wearable sensor. Dependence of the resistance (A), reactance (B), and phase (C) of the PANi/AgµFs composite on the reading frequency at different pH levels (2.8-8.6) (D) Nyquist plot of the PANi/AgµFs composite.

The resistance of PANi in the PANi EB form generally too high (~50 MΩ for the dimensions of the WPED) to be measured accurately, hampering the development of wearable, impedance-based pH sensors using PANi. To overcome this drawback, we optimized a PANi based polymer composite previously developed by our team to accurately measure pH over the clinical range of variation of most biofluids, such as sweat, vaginal fluid, wound exudate, gastroesophageal reflux, and/or urine. In this work, we enrich the PANi ES polymer with 200% (w/w) AgµFs. The high surface area and random orientation of the AgµFs enable the formation of efficient charge percolation networks through the PANi/AgµFs matrix, reducing its resistance to values (<10 MΩ) that can easily be measured using inexpensive, miniaturized instrumentation.

Figure 12:
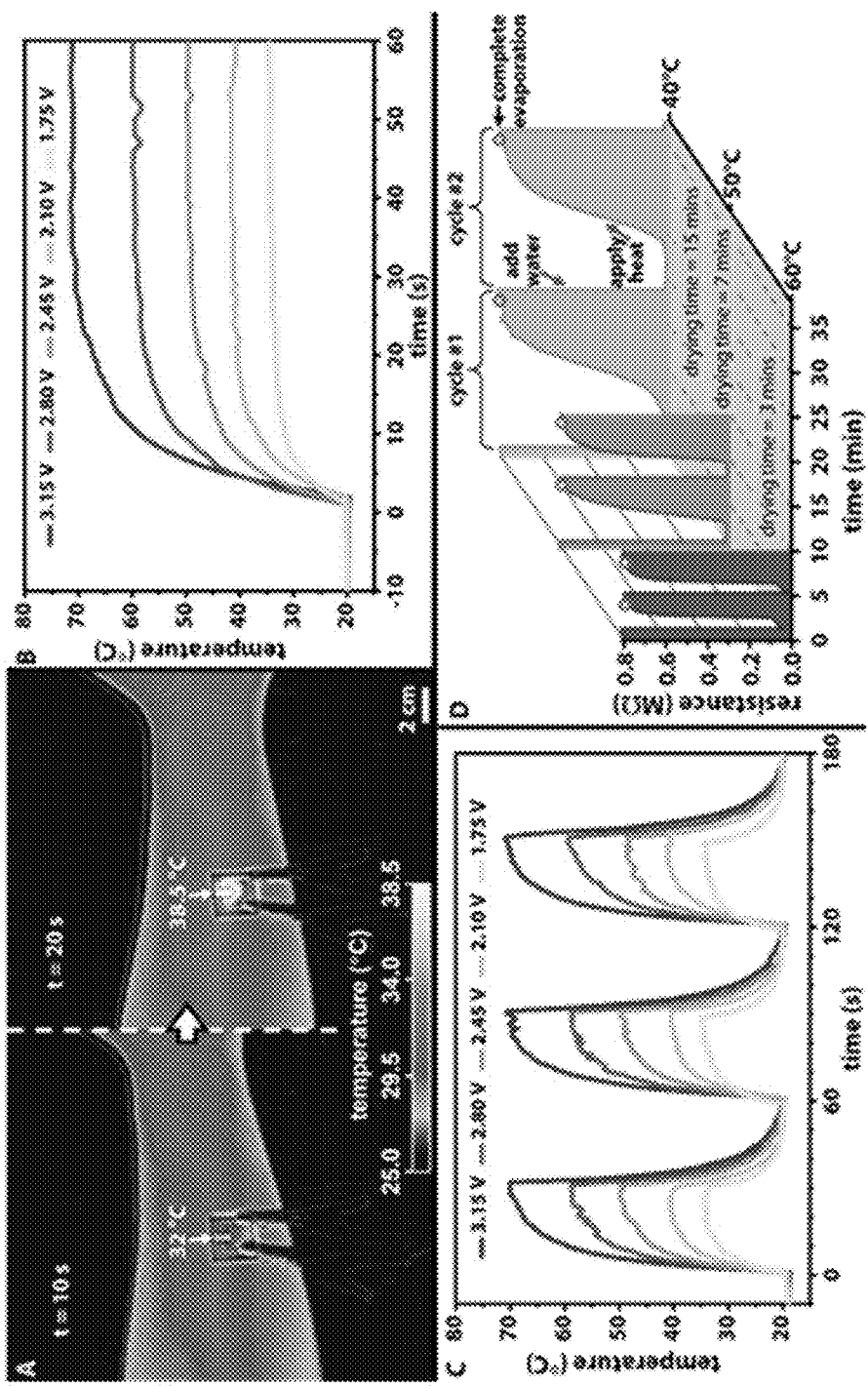
FIG. 12. Illustrates a characterization of a resistive heating element a wearable sensor.

To characterize the changes in the impedance of the PANi/AgµFs composite due to changes in environmental pH, an example embodiment of the device was exposed to various pH buffers (2.8-8.6) and measured their complex impedances across a broad range of frequencies (1 Hz-1 MHz). Graph A shows the dependence of the resistance (real component of the complex impedance) on the frequency for WPEDs exposed to different pH levels. The proposed PANi/AgµFs composite exhibits minimal dielectric dispersions at low pH values, since the concentration of AgµFs efficiently reduced the dielectric behavior of PANi. Even for high pH values (6-8), dielectric dispersions only appear at frequencies greater than 100 kHz, demonstrating that the PANi/AgµFs composite remains sensitive to pH changes over a larger frequency range than that of pure PANi. The reactance spectra (imaginary component of the complex impedance) shows a single peak at high frequencies (B). The shifting to higher frequencies of these reactance peaks, as well as their reduction in amplitude when acidity is increased, can be explained by the faster charge transfer in the protonated PANi ES/AgµFs composite. The increasing negative phase angles (Graph C) at higher pH values show the increasing capacitive character of the PANi/AgµFs composite as the conductivity of the PANi decreases. The Nyquist plots of the PANi/AgµFs composite shown in Graph D exhibit a single arc (in agreement with the single reactance peak), demonstrating FIG. 12. Illustrates a characterization of a resistive heating element in the wearable sensor 100. Graph A illustrates infrared thermography images demonstrating the use of the heating element of the device as a sweat stimulator by applying a constant voltage of 2.1 V. Graph B illustrates steady state temperatures achieved by the heater by applying different voltage levels (1.75 V-3.15 V). Graph C illustrates repeatability of temperatures achieved by the resistive heaters over multiple heating cycles for different voltage levels. Graph D illustrates a change in resistance of the device as it is consecutively wetted and then dried by the resistive heating element. The drying time reduces with increase of heater temperature which is achieved by increasing the heating voltage.

The heating layer of the WPEDs contains a resistive heating element lying on top of the PANi/AgµFs based pH sensor, separated by a non-conductive layer of EC. Graph A shows thermal infrared (TIR) images of an on-skin WPED with the active heating element in OFF and ON conditions. When turned on, the heater evaporates the analyte from the PANi/AgµFs sensor, ensuring that the measured impedance corresponds to the interaction between the pH of the biofluid being measured and the PANi/AgµFs composite. Additionally, the evaporation of the analyte from the pH sensing layer prevents the electrodes from being short-circuited. Since the heater is separated from the pH sensor by an ~10-µm-thick layer of EC, the temperature at the PANi/AgµFs composite reaches a steady state in ~10 s (Graph B). The temperature at the pH sensor can be controlled by tuning the voltage applied to the resistive element of the heating layer. Graph C shows the control and repeatability of the temperatures induced at the sensing layer over multiple heating cycles as well as its rapid cooling due to the efficient heat dissipation of WPEDs. We characterized the performance of the heaters by soaking the pH sensors with water and maintaining the heater at different temperatures until complete evaporation. During the application of heat, the wearable impedance analyzer continuously monitors the resistance of the pH sensor, identifying its drying to be complete when the increments in resistance become smaller than 5% in 30 s. We characterized the drying time of the pH biosensor sensor at different temperatures induced by the heating element of the WPED (Graph D). WPEDs, when used as skin-mounted devices, dry after maintaining a wearer-safe constant temperature of 40° C. for 15 mins. When used as ex-vivo pH sensors, WPEDs dry in only 3 min at 60° C.

Figure 13:
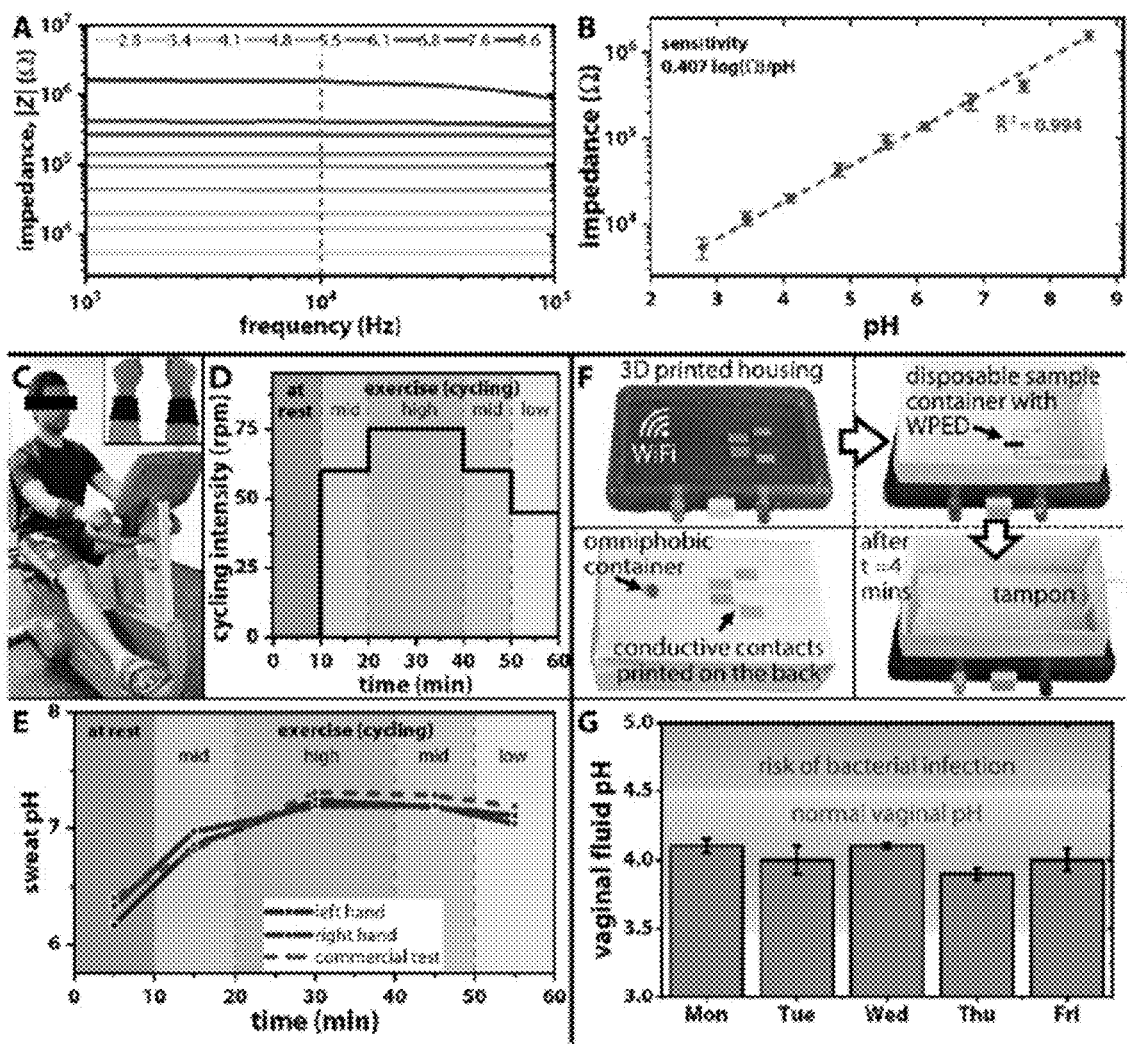
FIG. 13 Illustrates an example of monitoring pH of human sweat and vaginal fluid using a wearable sensor.

FIG. 13 Illustrates an example of monitoring pH of human sweat and vaginal fluid using the wearable sensor 100. Graph A illustrates a Bode plot for the magnitude of impedance measured by a WPED for different pH levels. The measured impedance is approximately constant across the frequency range of 1 kHz-10 kHz. Graph B illustrates a relationship between the modulus of the impedance of the PANi/AgµFs composite and pH. The calibration curve is obtained at a 10 kHz frequency, providing a sensitivity of 0.407 log(Ω)/pH with $R^2=0.994$. Error bars indicate standard deviation from 3 samples. Graph C illustrates a volunteer exercising on a stationary bicycle with two WPEDs with wearable impedance analyzers worn on both forearms to monitor sweat pH. Graph D illustrates the intensity of the exercise performed by the volunteer over one hour. Graph E illustrates the sweat pH values obtained from the volunteer over different phases of exercise. Graph F illustrates a portable WPED-based device for the at-home monitoring of vaginal pH. This point of care testing device comprises two components: A re-usable measuring base containing a wireless impedance analyzer and a single-use omniphobic paper-based box with a WPED attached to its bottom (Graph F). The electrical contacts of the WPED are folded so that they are in contact with the conductive pads printed on the measuring base, which enable the interfacing between the WPED and the impedance analyzer. We rendered the paper-box omniphobic using a fluoroalkyl organosilane. Prior to collecting measurements of the vaginal pH, a healthy female volunteer out of her menstrual cycle wore a sanitary tampon for 5 h. The tampon was simply placed on the omniphobic paper box and this box was placed on the measuring base during 5 mins. The collected measurement of vaginal pH was then wirelessly transmitted to a laptop computer through the app (Graph G). After the test is performed, the paper-based container holding both the tampon and the WPED can be easily disposed, maintaining the wireless measuring stage clean. Graph G illustrates the results obtained after measuring the pH of vaginal fluid of a volunteer measured over 5 consecutive days.

As illustrated in Graph C and Graph F, WPEDs in combination with a wearable or portable impedance analyzer, can monitor pH levels of sweat (Graph C) or simulated vaginal fluid (Graph F). In various examples, the impedance analyzers may operate at 10 kHz frequency to maximize the contrast between impedances due to different pH values (Graph D). Experimental result revealed that working frequencies higher than 10 kHz may result in impedance values decreasing with frequency, especially at high pH levels, due to the capacitive effects exhibited at those frequencies by the PANi/AgµFs composite.

Figure 14:
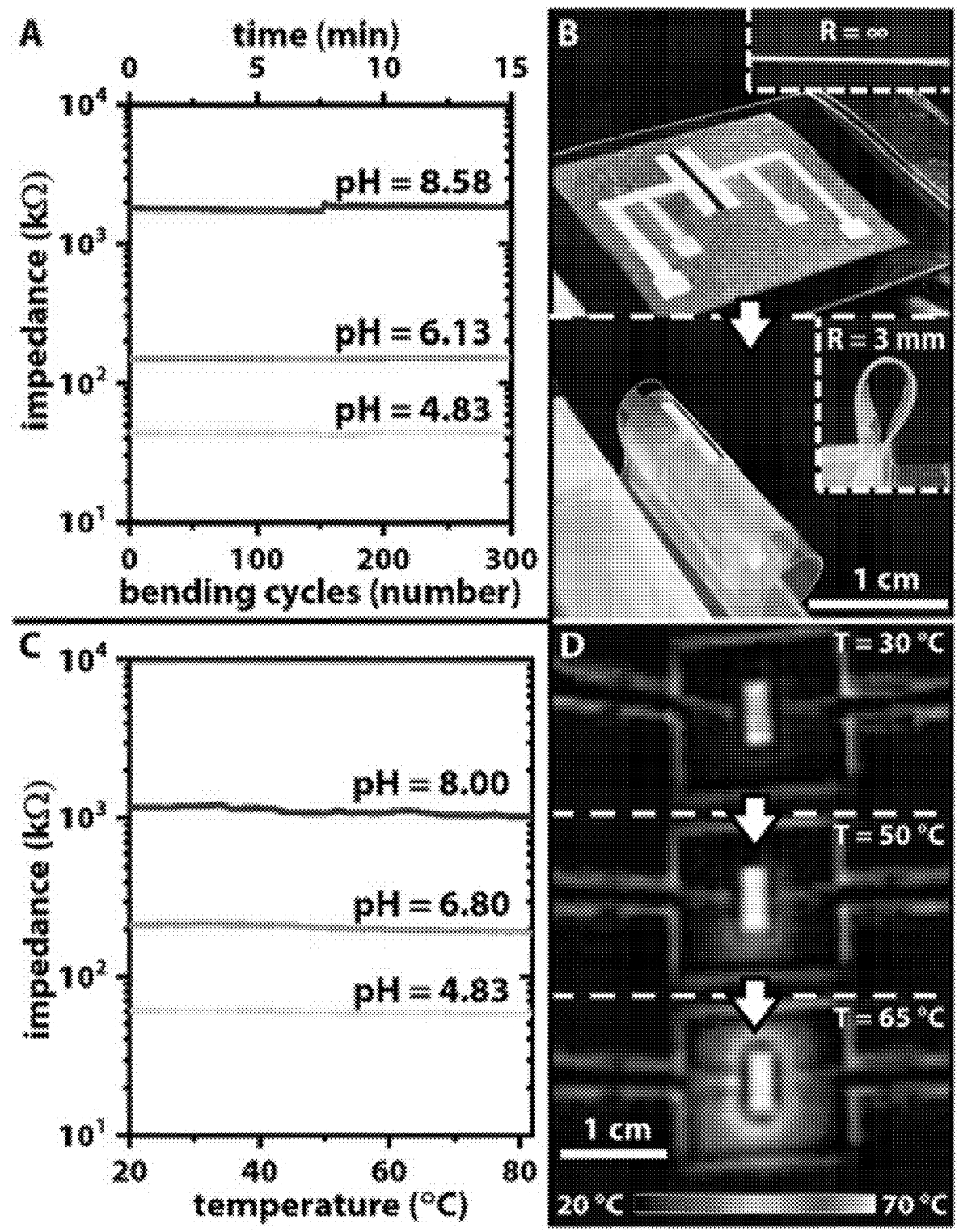
FIG. 14 illustrates mechanical and thermal stability of the pH measurements collected using waterproof electronic decals.

The impedance of the PANi/AgµFs composite depends on the relative composition of the two phases of PANi (PANi-EB and PANi-ES), which is regulated by the concentration of H+ ions. Since pH is defined as the decimal logarithm of the reciprocal of the H+ concentration, the logarithm of the impedance modulus exhibits a linear correlation with pH values (Graph E). Therefore, the relationship between the modulus of the impedance and pH may be described as:

$$\log_{10}|Z|=A+\beta \cdot pH,$$

where A and β are experimentally determined fitting parameters depending on the composition of the PANi/AgµFs composite and the design of the WPED (supplementary section S6 in appendix). Using experimental results obtained at 10 kHz (indicated by the dashed line in Graph D), the pH sensing capabilities of WPED are calibrated according to the following equation: $\log_{10}|Z|=2.64+0.407 \cdot pH$ (Graph E). This equation describes WPEDs across the 2.8-8.6 pH range, which covers the clinical range of variation of pH for vaginal fluid and sweat FIG. 14 illustrates mechanical and thermal stability of the pH measurements collected using WPEDs. Graph A illustrates mechanical stability of the pH sensors at three different pH values over 300 bending cycles. Graph B illustrates bending test positions, cycling from a flat configuration to a radius of curvature of 3 mm. Graph C illustrates effect of temperature variation on the pH response of WPED at three different pH values. Graph D illustrates TIR images showing the temperature of the WPED as it is heated by the heater.

WPEDs may be transferred to highly deformable platforms—such as skin or conventional hygiene products—to monitor pH levels. Therefore, the usability of WPEDs depends on their ability to maintain their accuracy under mechanical deformation. Graph A shows the insensitivity of the analytical performance of the pH sensor to 300 loading and unloading cycles, where the WPED was bent to a radius of curvature of 3 mm (Graph B) and then returned to its flat configuration. Additionally, we observed no thermal drifts on the pH measurements caused by the temperature induced on the PANi/AgµFs composite by the heating element of the WPEDs (Graph C-D). The thermal stability of the PANi/AgµFs pH sensor spans over the range 20-80° C. This demonstrates that the application of heat to induce sweat or dry the pH sensor (40° C. on skin, 60° C. on tampons) does not compromise the accuracy of WPEDs.

Thus, low cost fabrication of highly conformal, waterproof electronic decals (WPEDs) that can be easily mounted on skin or sanitary tampons to monitor sweat and vaginal pH. The sensing layer of the WPEDs comprising a pH sensitive PANi/AgµFs composite the impedance range of which is optimized to avoid thermal drift (0.06%/° C.) and match the low currents typically provided by low power wearable electronics, exhibiting a pH sensitivity of 0.407 log(Ω)/pH. An independent resistive heating element on top of the PANi/AgµFs composite serves to stimulate sweating (for sweat pH monitoring WPEDs) and evaporate excess of fluid in the PANi/AgµFs composite, avoiding short circuits and reducing the variability of the measurements. WPEDs have five significant advantages over previously reported sweat pH sensors: (i) The flexibility, low thickness, and self-adhesive behavior of WPEDs facilitate their conforming to curved and irregular substrates, eliminating the somatosensory perception of these electronic decals when mounted on skin; (ii) the decoupling between the disposable WPEDs and a reusable wireless impedance analyzer with integrated data processing and transmission modules, enables the use of WPED as single use biosensors at the point of care. A user friendly mobile App receives, displays, encrypts, and stores the results of the pH measurements, informing the patient and transferring the data to relevant care givers so that they can provide early preventive treatment; (iii) the transparency and the breathability of WPEDs makes them barely perceptible and prevent skin irritation even when the same sensor is worn for up to 8 h; (iv) the lamination of the contact pads, and the sensing and stimulating elements of the WPED with biocompatible polymers prevents metals from contacting the skin of sensitized users, further minimizing skin irritation; (v) WPEDs are moisture insensitive and exhibit high thermal and mechanical stability, conforming to the natural motions of the wearer in a variety of environments. The reported WPEDs and the wearable and portable impedance analyzers, at their present level of development, also have two limitations: (i) A measuring time of ~10 mins is required to measure sweat pH as the heater is limited to 42° C., the maximum temperature which can be safely applied to the skin of the user; (ii) when using WPEDs to identify vaginal infections during menstrual periods, it needs to be taken into account that the presence of blood (pH~7.4) will naturally increase the pH of vaginal fluid. WPEDs, however, are simple to apply and to interface and can allow the accurate wireless monitoring of pH over the clinical range of a variety of biofluids such as sweat, vaginal fluid, wound exudate, or gastroesophageal reflux. We expect that WPEDs, with further development, will be able to expand the sensing capabilities in home environments and at the point of care, and also be useful in various industrial applications, such as monitoring food and dairy quality.

While various embodiments have been described, it will be apparent to those of ordinary skill in the art that many more embodiments and implementations are possible. Accordingly, the embodiments described herein are examples, not the only possible embodiments and implementations.

A second action may be said to be "in response to" a first action independent of whether the second action results directly or indirectly from the first action. The second action may occur at a substantially later time than the first action and still be in response to the first action. Similarly, the second action may be said to be in response to the first action even if intervening actions take place between the first action and the second action, and even if one or more of the intervening actions directly cause the second action to be performed. For example, a second action may be in response to a first action if the first action sets a flag and a third action later initiates the second action whenever the flag is set.

To clarify the use of and to hereby provide notice to the public, the phrases "at least one of <A>, <B>, . . . and <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed.

What is claimed is:

1. A wearable sensor decal comprising
a flexible wrapper layer;
a porous film layer;
a first plurality of electrodes positioned on the flexible wrapper layer;
a heating element positioned on the flexible wrapper layer and conductivity coupled to the first plurality of electrodes;
an intermediate layer on top of the heating element and on top of at least a portion of the first plurality of electrodes;
a second plurality of electrodes at least partially positioned on top of the intermediate layer and extending across an edge of the intermediate layer and onto the flexible wrapper layer; and
a biosensor positioned on the intermediate layer and conductively coupled to the second plurality of electrodes,
wherein the first plurality of electrodes, the heating element, the second plurality of electrodes, and the biosensor are each at least partially disposed between the flexible wrapper layer and the porous film layer,
wherein the intermediate layer separates the heating element from the biosensor, and
wherein the porous film layer is hydrophilic to allow biofluids pass to the biosensor.

2. The wearable sensor decal of claim 1, wherein the biosensor and the heating element are aligned with each other on either side of the intermediate layer.

3. The wearable sensor decal of claim 1, wherein the intermediate layer comprises ethyl cellulose (EC).

4. The wearable sensor decal of claim 1, wherein the flexible wrapper layer is hydrophobic.

5. The wearable sensor decal of claim 1, wherein the flexible wrapper layer, the intermediate layer, and the porous film layer are permeable to water vapor.

6. The wearable sensor decal of claim 1, wherein the biosensor is a pH sensor.

7. The wearable sensor decal of claim 1, wherein the biosensor comprises emeraldine salt polyaniline (PANi ES).

8. The wearable sensor decal of claim 1, wherein the first plurality of electrodes and/or second plurality of electrodes are Ag/AgCl electrodes.

9. The wearable sensor decal of claim 1, wherein the porous film layer comprises porous ethyl cellulose (p-EC).

10. The wearable sensor decal of claim 1, wherein the flexible wrapper layer comprises ethyl cellulous and polydimethylsiloxane (PDMS).

11. The wearable sensor decal of claim 1, wherein the flexible wrapper layer is deposited on a sacrificial polyvinyl alcohol (PVA) coated paper.

12. The wearable sensor decal of claim 1, wherein the porous film layer is configured to be received by a target surface on a first side of the wearable sensor decal.

13. The wearable sensor decal of claim 12, wherein respective portions of the first plurality of electrodes and respective portions of the second plurality of electrodes are exposed on second side of the wearable sensor decal opposite the first side.

14. A method, comprising:
depositing a hydrophobic wrapper layer onto a sacrificial layer;
depositing a plurality of first electrodes onto the wrapper layer;
depositing a heating element onto the wrapper layer, the heating element conductively coupled with the first electrodes;

depositing an intermediate layer onto at least a portion of the wrapper layer, the heating element, the first electrodes, or a combination thereof;

depositing a plurality of second electrodes onto the intermediate layer and the wrapper layer;

depositing a biosensor onto the intermediate layer, the wrapper layer, or a combination thereof, the biosensor conductively coupled to the second electrodes; and depositing a hydrophilic film to cover the biosensor and at least a portion of the second electrodes.

15. The method of claim 14, wherein depositing the first electrodes further comprises, printing conductive ink onto the wrapper layer, wherein depositing the second electrodes further comprises, printing conductive ink onto the intermediate layer and the wrapper layer.

\* \* \* \* \*